United States Patent [19]

Yugari et al.

[11] 3,950,223
[45] Apr. 13, 1976

[54] STABILIZING AND ENHANCING UROKINASE ACTIVITY

[75] Inventors: Yasumi Yugari, Kamakura; Kenji Takezawa, Yokohama, both of Japan

[73] Assignee: Ajinomoto Co., Inc., Tokyo, Japan

[22] Filed: Dec. 7, 1973

[21] Appl. No.: 422,789

[30] Foreign Application Priority Data
Dec. 7, 1972  Japan............................ 47-122809

[52] U.S. Cl.................. 195/68; 195/63; 195/66 B
[51] Int. Cl.$^2$........................................ C07G 7/02
[58] Field of Search...................... 195/63, 68, 66 B

[56] References Cited
UNITED STATES PATENTS

| | | | |
|---|---|---|---|
| 2,806,815 | 9/1957 | Singher et al............... | 195/63 |
| 3,050,445 | 8/1962 | Damaskus et al............ | 195/63 |
| 3,272,717 | 9/1966 | Fukumoto et al. .......... | 195/63 X |
| 3,274,059 | 9/1966 | Richard ...................... | 195/63 X |
| 3,540,984 | 11/1970 | Deutsch....................... | 195/63 X |

OTHER PUBLICATIONS

White et al., Urinary Plasminogen Activator (Urokinase), Methods in Enzymology, Vol. XIX, 1970, (pp. 665–672).

*Primary Examiner*—David M. Naff
*Attorney, Agent, or Firm*—Cooper, Dunham, Clark, Griffin & Moran

[57] ABSTRACT

The activity of urokinase in aqueous solution is stabilized and enhanced by addition of water soluble amines selected from the group consisting of amino sugars, amino acids and cationic surfactants.

6 Claims, No Drawings

STABILIZING AND ENHANCING UROKINASE ACTIVITY

This invention relates to a method for stabilizing and enhancing urokinase activity in urokinase containing aqueous media and to the improved forms of urokinase so produced. More particularly, the invention relates to a method for enhancing and stabilizing urokinase activity in aqueous media at a pH of from 4 to 11 by the addition of at least one water soluble amine. The pH of the solution often is not appreciably affected by the addition of the selected amine. It may, however, be maintained within the desired range by the addition of an alkaline or acid reagent. Alkali metal hydroxides and mineral acids are most practical. Sodium hydroxide and hydrochloric acid are preferred.

Urokinase is an enzyme which is found in urine. It is known to stimulate the production of the proteolytic enzyme plasmin which is important for dissolving blood clots. Urokinase therefore is of known and significant importance in the treatment of disorders which cause the formation of blood clots in the cardiovascular system.

The amount of urokinase present in urine is extremely small and its isolation therefore is particularly tedious and expensive. Moreover, urokinase is very unstable in aqueous solution and tends rapidly to lose its activity. This loss of activity which appears to take place through decomposition of the urokinase is especially rapid at a hydrogen ion concentration sufficient so that the pH is less than 4 or greater than 11. However, even if the pH is maintained at from 4 to 11, there is appreciable and fairly rapid loss of urokinase activity in any aqueous solution containing it. This loss of activity is also noticeable with urokinase in the solid form which is intended for therapeutic use, for example, in an aqueous media.

It has now been found that the urokinase activity of aqueous solutions containing it at a pH of from 4 to 11 can be significantly enhanced by the addition of a water soluble amine. The amount of amine added should not exceed the quantity necessary to modify the pH outside of this range. It has been found moreover, that the improved activity can be maintained for an appreciable period of time. Furthermore, even when the urokinase is recovered from an aqueous solution containing it together with the added amine, the activity of the isolated product is stabilized and enhanced compared to urokinase products isolated from aqueous media which do not contain the added amine.

While a number of water soluble amines are useful in the process of this invention, the preferred amines are amino sugars, amino acids and cationic surfactants which are known as quaternary ammonium salts.

Any of a variety of amino acids may be used in the process of this invention. The preferred amino acids are the naturally occurring L-form amino acids, particularly proline, arginine, lysine, histidine, threonine, tryptophan, glutamine, methionine, serine, citrulline, ornithine, tyrosine and hydroxyproline. Anthranilic acid, sulfanilic acid, homoserine and hydroxylysine are also suitable.

The amount of amino acid which will normally be added to the selected urokinase containing aqueous media will normally be more than $10^{-4}$ molar and may be appreciably higher. As a practical matter, relatively small quantities of the amino acid will be added since there is little advantage to be gained by the addition of excessive amounts. They may be added in the form of their non-toxic salts, particularly organic and inorganic acid addition salts. The most convenient salt form is normally the hydrochloride.

Although other amino sugars can be employed in the practice of this invention, the most convenient members of this class are hexosamines, particularly glucosamine, galactosamine, mannosamine and their acyl derivatives such as N-acetyl-D-glucosamine. The D-forms of the amino sugars are especially useful.

Normally the concentration of amino sugar in the aqueous media will be at least $10^{-5}$ molar.

Cationic surfactants which may be utilized in the process of the invention may be selected from the class including:

tetraalkylammonium salts
cethyltrimethylammonium salts
stearyl-trimethyl-ammonium salts
higher alkyl-aralkyl quaternary ammonium salts
higher alkyl-dimethyl-benzyl-ammonium salts
dimethyl-benzyl-lauryl ammonium salts
higher alkyl aryl quaternary ammonium salts
higher alkyl-dimethyl-phenyl ammonium salts
aryl-aralkyl-alkyl-quaternary ammonium salts
dimethyl-phenyl-benzyl ammonium salts
higher alkylpyridinium salts
laurylpyridinium salts
polyalkyl-naphthalene methylpyridinium salts In this classification, alkyl normally means lower alkyl containing for example up to 6 carbon atoms, and higher alkyl refers to alkyl groups containing from about 11 to 20 carbon atoms. Aryl is normally a phenyl group. Quaternary ammonium salts which are commercially available and particularly useful in the invention include:

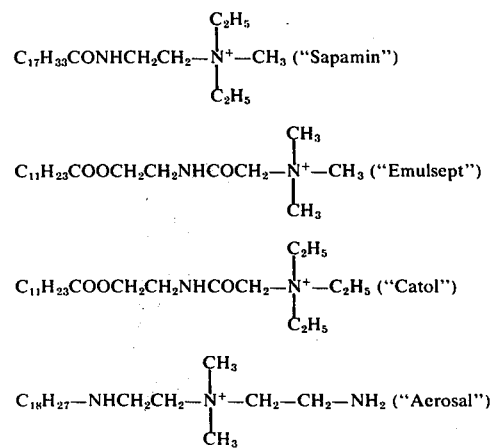

The quantity of cationic surfactant amine added to the aqueous solution will normally be of the order of from $1 \times 10^{-3}$ to $1 \times 10^{-1}$ weight percent based on the total weight, although appreciable variation from the range can be tolerated, especially in the presence of impurities, without adverse effect. If this type of surfactant is selected as the stabilizing agent, it is best to determine the optimum concentration by treatment of small aliquots of the solution with various concentrations of surfactants. The concentration of surfactant should not be high enough so as to cause denaturation of the urokinase.

A large number of urokinase containing aqueous media are known and have been described for various purposes. These include, for example, urine, filtered urine and various solutions obtained during normal isolation and purification procedures for urokinase including for example relatively concentrated or dilute aqueous solutions containing urokinase in various degrees of purity, acidic and alkaline solutions of urokinase. All of these solutions are susceptible to use in this invention, provided that the pH is maintained in the defined range.

The stabilizing compound or mixture of compounds can be added to aqueous media containing urokinase at any stage in the standard methods for the isolation and purification of the urokinase. These include, for example, solutions containing urokinase equilibrated with an absorbent such as a modified dextran, buffered urokinase solutions used in dialysis procedures and solutions from which the urokinase is precipitated.

It has been observed that the enhanced and stabilized activity of the urokinase is maintained even when the urokinase is recovered. It appears that the improved form of urokinase produced by the process of this invention is one in which the amine is adsorbed to the surface of the urokinase molecule.

The activity of urokinase is determined by the following method which is a modification of the method described by Walton in Biochem. Biophys. Acta. Vol. 132, 104 (1967).

0.11 M N-acetyl-glycyl-L-lysine methylester are dissolved in 1.5 KCl. 0.11 ML of this solution are mixed with urokinase and incubated at 37°C. During the incubation, a pH of the reaction mixture is maintained at pH 6.90 by adding standard caustic soda solution. Consumed caustic soda is calculated and activity (esterolytic activity) is calculated as follows:

$1.0 \times 10^{-2} \mu$ moles NaOH / min = 8.0 plougs unit the activity determined by the method as above are the same as fibrinolytic activity referred to in Biochem. Biophys. Acta. Vol. 24, 278 (1957).

A brief explanation of the meaning of "stabilizing and enhancing urokinase activity" as used in this invention may be helpful. When urokinase activity in an aqueous solution containing it is measured by the preceding above procedures, it will be found to have a certain value at a particular point in time. As the solution ages, this value decreases more or less rapidly, depending upon the particular medium. If this same solution is treated in accordance with this invention, it will be found that at any point in time during the time interval study urokinase activity is higher than the activity of the untreated medium. Moreover, the useful life of the treated solution is longer than the useful life of the untreated solution. The same results are observed with urokinase preparations isolated from treated and untreated solutions. That is, the useful activity at a particular point in time for the product isolated from the treated solution is greater than that of the product isolated from the untreated solution. Moreover, this useful activity persists for a longer period of time.

The following non-limiting examples are given by way of illustration.

EXAMPLE 1

Fresh human urine was dialyzed against deionized water with Sephadex G-25, and to the dialyzed urine, the compounds as shown in Table 1 were added. Urokinase activity as measured by the modified Walton method compared with the untreated product taken as 100 percent is shown in Table I.

Table I

| Compound | Amount Added | Urokinase Activity (%) |
|---|---|---|
| none | — | 100 |
| amino acids | | |
| L-proline | $1 \times 10^{-2}$ M | 130 |
| L-hydroxyproline | " | 140 |
| L-arginine HCl | " | 130 |
| L-lysine HCl | " | 140 |
| L-histidine.HCl | " | 180 |
| L-citrulline | " | 130 |
| L-threonine | " | 130 |
| L-serine | " | 120 |
| L-methionine | " | 130 |
| L-cysteine | " | 130 |
| L-valine | " | 120 |
| L-tyrosine | " | 120 |
| L-tryptophane | " | 140 |
| L-glutamine | " | 130 |
| L-glutamic acid | " | 130 |
| D-tryptophan | " | 140 |
| γ-aminobutylic acid | " | 130 |
| anthramilic acid | " | 130 |
| sulphanilic acid | " | 130 |
| amino sugars | | |
| D-glucosamine.HCl | " | 170 |
| D-galactosamine.HCl | " | 150 |
| D-mannosamine.HCl | " | 170 |
| N-acetyl-D-glucosamine | " | 200 |
| Cationic surfactant | | |
| benzalkonium chloride | 0.03 g/dl | 180 |
| benzethonium chloride | 0.001 g/dl | 200 |
| trimethylstearyl-ammonium chloride | 0.03 g/dl | 130 |
| laurylpyridinium chloride | 0.03 g/dl | 120 |
| "Sapamine MS" | 0.03 g/dl | 130 |

EXAMPLE 2

The amounts of the compounds added to the same dialyzed urine as in Example 1 were changed as shown in Table II, and urokinase activity was measured.

TABLE II

| Compound, Amount Added | | Urokinase Activity |
|---|---|---|
| — | | 100 (%) |
| L-histidine | | |
| | $1 \times 10^{-5}$ M | 100 |
| | $1 \times 10^{-4}$ M | 120 |
| | $1 \times 10^{-3}$ M | 180 |
| | $1 \times 10^{-2}$ M | 180 |
| | $1 \times 10^{-1}$ M | 190 |
| D-glucosamine | | |
| | $1 \times 10^{-5}$ M | 100 |
| | $1 \times 10^{-4}$ M | 120 |
| | $1 \times 10^{-3}$ M | 160 |
| | $1 \times 10^{-2}$ M | 170 |
| | $1 \times 10^{-1}$ M | 180 |
| N-acetyl-D-glucosamine | | |
| | $1 \times 10^{-5}$ M | 100 |
| | $1 \times 10^{-4}$ M | 110 |
| | $1 \times 10^{-3}$ M | 150 |
| | $1 \times 10^{-2}$ M | 200 |
| | $1 \times 10^{-1}$ — | 200 |
| benzalkonium chloride | | |
| | 0.1 mg/dl | 100 |
| | 1.0 mg/dl | 110 |
| | 10 mg/dl | 150 |
| | 30 mg/dl | 180 |
| | 100 mg/dl | 190 |
| | 300 mg/dl | 0 |
| benzethonium chloride | | |
| | 0.01 mg/dl | 100 |
| | 0.1 mg/dl | 150 |
| | 1.0 mg/dl | 200 |
| | 10 mg/dl | 61 |
| | 100 mg/dl | 23 |

EXAMPLE 3

Urokinase (2,000 p.u./mg. protein) was dissolved in water, dialyzed with Sephadex G-25. The dialyzed urokinase solution was diluted with water to contain 10 p.v/ml urokinase, and filtered through a Millipore filter (0.45 $\mu$). The filtered solution was treated with the compound shown in Table III and allowed to stand at ambient temperature for the periods shown.

TABLE III

| Compound, Amount Added | Hours | Urokinase Activity (%) |
|---|---|---|
| none | 0 | 100 |
| | 12 | 50 |
| | 24 | 30 |
| | 48 | 10 |
| | 72 | 0 |
| L-histidine HCl | 0 | 190 |
| ($1 \times 10^{-2}$ M) | 12 | 190 |
| | 24 | 180 |
| | 48 | 160 |
| | 72 | 140 |
| D-glucosamine.HCl | | |
| ($1 \times 15 \cdot 2$ M) | 0 | 180 |
| | 12 | 180 |
| | 24 | 180 |
| | 48 | 170 |

TABLE III-continued

| Compound, Amount Added | Hours | Urokinase Activity (%) |
|---|---|---|
| | 72 | 160 |
| benzalkonium chloride | | |
| (0.03 g/dl) | 0 | 200 |
| | 12 | 200 |
| | 24 | 200 |
| | 48 | 190 |
| | 72 | 190 |

EXAMPLE 4

The same filtrates of the urokinase solution of Example 2 were allowed to stand for a day. The urokinase activities which were measured are recorded in Table IV.

Table IV

| Compound (Amount Added) | Urokinase Activity (%) |
|---|---|
| none | 30 |
| L-lysine.HCl ($1 \times 10^{-2}$ M) | 120 |
| D-galactosamine.HCl ($1 \times 10^{-3}$ M) | 140 |
| D-mannosamine.HCl ($1 \times 10^{-3}$ M) | 160 |
| N-acetyl-D-glucosamine ($1 \times 10^{-2}$ M) | 200 |
| benzalkonium chloride (0.03 g/dl) | 170 |
| benzethonium chloride (0.001 g/dl) | 180 |
| trimethylstearylammonium chloride (0.03 g/dl) | 130 |
| laurylpyridinium chloride (0.03 g/dl) | 120 |

EXAMPLE 5

Fresh human urine (7.0 p.u. 1 ml) was filtered through a Millipore filter (0.45 $\mu$), and the compounds shown in Table V were added to the filtered urine. The observed activities of the filtered urine are shown in Table V.

Table V

| Compound | Amount Added | Urokinase Activity (%) |
|---|---|---|
| none | — | 100 |
| L-lysine HCl | $1 \times 10^{-2}$ M | 150 |
| L-threonine | $1 \times 10^{-2}$ M | 130 |
| glucosamine | $1 \times 10^{-3}$ M | 200 |
| benzoalkonium chloride | 0.1 g/dl | 280 |

EXAMPLE 6

Fresh human urine (7.0 p.u./ml), was filtered through a Millipore filter and was treated with one of the compounds as in Table VI, and dialyzed against water with Sephadex G-25. Urokinase activity before and after the dialysis are shown in Table VI.

Table VI

| Compound | | Urokinase Activity (%) |
|---|---|---|
| none | — | 100 |
| | + | 100 |
| L-lysine.HCl | — | 130 |
| ($1 \times 10^{-2}$ M) | + | 120 |
| D-glucosamine | — | 180 |
| ($1 \times 10^{-2}$ M) | + | 170 |
| dihydrostreptomycin sulfate | — | 210 |
| ($2 \times 10^{-1}$ M) | + | 210 |
| benzalkonium chloride | — | 180 |
| (0.03 g/dl) | + | 180 |

—not dialyzed.
+dialyzed.

EXAMPLE 7

Fresh human urine was charged on carboxyl methyl cellulose column which was previously equilibrated with 0.01 M sodium phosphate, —0.1 M sodium chloride buffer (pH 7.2), (buffer I), and urokinase was absorbed on carboxy methyl cellulose. The column was washed with buffer I further containing 0.001 g/dl benzalkonium chloride, allowed to stand for 1 day, and thereafter urokinase was eluted with 0.3 M sodium chloride — 0.3 M sodium hydroxide (pH 11.0) buffer. The recovery of urokinase in the eluate was 180 percent. While, when the column was washed with buffer I, free from the quaternary salt and urokinase was eluted by the same method as above, recovery of urokinase was 37 percent.

EXAMPLE 8

Fresh human urine was passed through a Sephadex G-25 column. The eluate obtained (urokinase activity 7.0 p.u./ml) was treated with one of 0.01 M NaCl, 0.03 g/dl benzalkonium chloride, $1 \times 10^{-2}$ M D-glucosamine or $1 \times 10^{-2}$ L-lysine, while maintaining the pH of the eluate by adding 0.1 N NCl or 0.1 N NaOH the pH as indicated in Table VII. After allowing the eluates to stand for 1 hour at ambient temperature, the urokinase activities in the eluates were determined. The results are shown in the following Table.

Table VII

| Compound Added | pH | Urokinase Activity (%) |
|---|---|---|
| NaCl | 3.0 | 100 |
|  | 4.0 | 100 |
|  | 7.0 | 100 |
|  | 8.0 | 100 |
|  | 10.0 | 96 |
|  | 11.0 | 50 |
| benzalkonium.chloride | 3.0 | 180 |
|  | 4.0 | 180 |
|  | 7.0 | 180 |
|  | 10.0 | 180 |
|  | 11.0 | 160 |
| D-glucosamine | 3.0 | 180 |
|  | 4.0 | 180 |
|  | 7.0 | 180 |
|  | 10.0 | 180 |
|  | 11.0 | 160 |
| L-lysine | 3.0 | 140 |
|  | 4.0 | 140 |
|  | 7.0 | 140 |
|  | 10.0 | 140 |

What is claimed is:

1. A method which comprises adding a water soluble amine selected from the group consisting of amino sugars and cationic surfactants to an aqueous media containing urokinase while maintaining the pH at from 4 to 11 in an amount sufficient to stabilize and enhance the urokinase activity in said media;
   a. the amino sugars being selected from the group consisting of hexosamines and N-acyl derivatives thereof;
   b. the cationic surfactants being selected from the group consisting of
      tetraalkylammonium salts
      cethyltrimethylammonium salts
      stearyl-trimethyl-ammonium salts
      higher alkyl-aralkyl quaternary ammonium salts
      higher alkyl-dimethyl-benzyl-ammonium salts
      dimethyl-benzyl-lauryl ammonium salts
      higher alkyl aryl quaternary ammonium salts
      higher alkyl-dimethyl-phenyl ammonium salts
      aryl-aralkyl-alkyl-quaternary ammonium salts
      dimethyl-phenyl-benzyl ammonium salts
      higher alkylpyridinium salts
      laurylpyridinium salts and
      polyalkyl-naphthalene methylpyridinium salts,
      wherein said alkyl group is a lower alkyl group containing up to 6 carbon atoms or a higher alkyl group containing from about 11 to 20 carbon atoms, and said aryl group being phenyl.

2. A method as in claim 1 further including the step of recovering the stabilized urokinase.

3. A method which comprises adding a water soluble amino sugar to an aqueous media containing urokinase while maintaining the pH at from 4 to 11 in an amount sufficient to stabilize and enhance the urokinase activity in said media; the amino sugar being selected from the group consisting of D-glucosamine, D-galactosamine, D-mannosamine, and N-acetyl D-glucosamine.

4. A method as in claim 3 wherein the amino sugar is D-glucosamine.

5. A method which comprises adding a water soluble cationic surfactant to an aqueous media containing urokinase while maintaining the pH at from 4 to 11 in an amount sufficient to stabilize and enhance the urokinase activity in said media; the cationic surfactant being selected from the group consisting of
   benzalkonium chloride
   benzelthonium chloride
   trimethylstearyl ammonium chloride
   laurylpyridinium chloride, and
   quaternary ammonium salts,
the cations of which are represented by the formulas

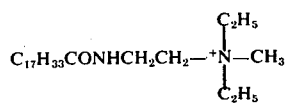

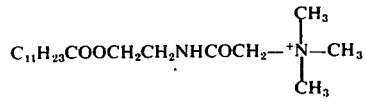

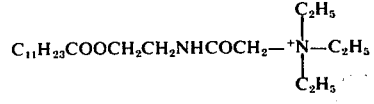

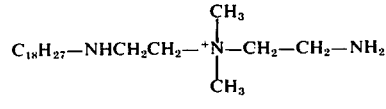

6. A method as in claim 5 wherein the cationic surfactant is benzethonium chloride.

\* \* \* \* \*